(12) United States Patent
Chakrabarti et al.

(10) Patent No.: US 10,836,698 B2
(45) Date of Patent: Nov. 17, 2020

(54) PROCESS FOR PREPARING METHACROLEIN

(71) Applicant: Rohm and Haas Company, Collegeville, PA (US)

(72) Inventors: Reetam Chakrabarti, Phoenixville, PA (US); Charles Como, Mount Laurel, NJ (US); Sarah L. Hruby, Kristianstad (SE); Dmitry A. Krapchetov, Lansdale, PA (US); Minh N. Ngo, Philadelphia, PA (US); Muhunthan Sathiosatham, Chalfont, PA (US); Mark A. Silvano, Upper Black Eddy, PA (US)

(73) Assignee: Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/614,512

(22) PCT Filed: May 24, 2018

(86) PCT No.: PCT/US2018/034275
§ 371 (c)(1),
(2) Date: Nov. 18, 2019

(87) PCT Pub. No.: WO2018/217964
PCT Pub. Date: Nov. 29, 2018

(65) Prior Publication Data
US 2020/0181053 A1    Jun. 11, 2020

Related U.S. Application Data

(60) Provisional application No. 62/525,257, filed on Jun. 27, 2017, provisional application No. 62/510,984, filed on May 25, 2017.

(51) Int. Cl.
| | |
|---|---|
| *C07C 45/50* | (2006.01) |
| *C07C 45/82* | (2006.01) |
| *C07C 67/40* | (2006.01) |
| *C07C 45/75* | (2006.01) |
| *C07C 47/22* | (2006.01) |

(52) U.S. Cl.
CPC ............. *C07C 45/75* (2013.01); *C07C 45/82* (2013.01); *C07C 47/22* (2013.01)

(58) Field of Classification Search
CPC ......... C07C 45/50; C07C 45/75; C07C 45/82; C07C 67/40
See application file for complete search history.

(56) References Cited

U.S. PATENT DOCUMENTS

| | | |
|---|---|---|
| 4,249,019 A | 2/1981 | Tamura et al. |
| 4,427,486 A | 1/1984 | Green et al. |
| 4,496,770 A | 1/1985 | Duembgen et al. |
| 4,518,796 A | 5/1985 | Aoshima et al. |
| 4,716,250 A | 12/1987 | Abatjoglou et al. |
| 4,731,486 A | 3/1988 | Abatjoglou et al. |
| 5,087,763 A | 2/1992 | Sorensen |
| 5,288,916 A | 2/1994 | Lorenz et al. |
| 5,892,102 A | 4/1999 | Mikami et al. |
| 5,969,178 A | 10/1999 | Okamoto et al. |
| 6,040,472 A | 3/2000 | Yamamatsu et al. |
| 6,107,515 A | 8/2000 | Yamaguchi et al. |
| 7,141,702 B2 | 11/2006 | Deshpande et al. |
| 2016/0200660 A1 | 7/2016 | Krill et al. |
| 2016/0229779 A1 | 8/2016 | Hoy, IV et al. |

*Primary Examiner* — Sikarl A Witherspoon
(74) *Attorney, Agent, or Firm* — Brian L. Mutschler

(57) ABSTRACT

Provided is a process for preparing dry methacrolein which maximizes capture of methanol. Also provided is a process for producing methyl methacrylate.

8 Claims, 1 Drawing Sheet

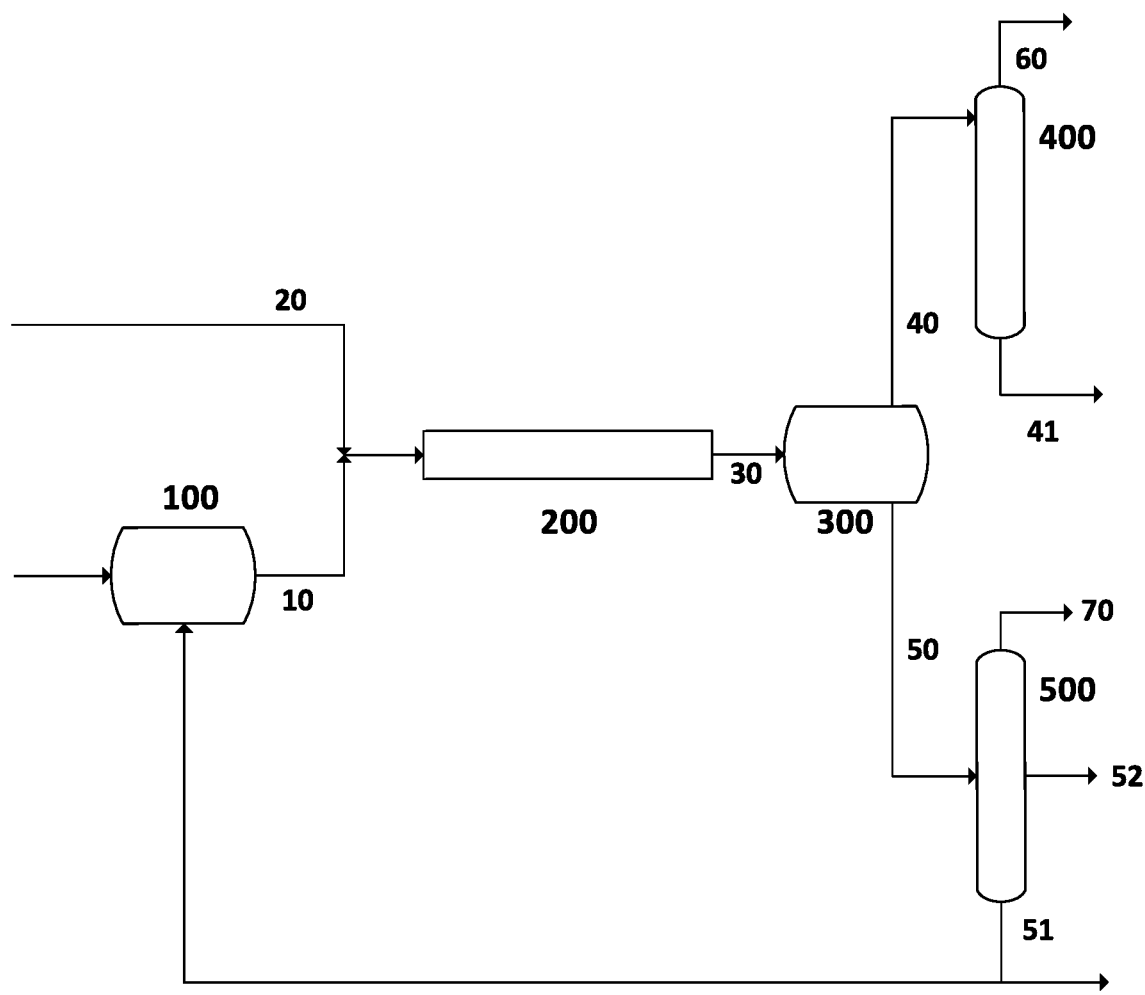

PROCESS FOR PREPARING METHACROLEIN

FIELD OF THE INVENTION

This invention relates to a process for preparing dry methacrolein, and to a process for making methyl methacrylate.

BACKGROUND

Methacrolein (2-methylprop-2-enal; "MA") is a common intermediate in methyl methacrylate ("MMA") production. MA can be produced from ethylene ($C_2$) feedstock, such as via liquid phase propionaldehyde condensation as disclosed in U.S. Pat. No. 4,496,770. The MA product stream contains methanol that is supplied with formaldehyde that is used in the propionaldehyde condensation. Such methanol can be advantageous in a subsequent oxidative esterification ("OER") process, which converts MA in the presence of methanol to MMA in a single step, as disclosed in U.S. Pat. Nos. 5,969,178, 6,107,515, and 6,040,472. However, the MA product stream also contains water, which can be detrimental to the subsequent OER process. Thus, a MA stream from conventional processes must be sufficiently dry to be used as a feed stream for a downstream OER process, in addition to containing sufficient methanol and having a substantial absence of certain impurities (e.g., propionaldehyde, formaldehyde, acetic acid, and organic heavies including, but not limited to, propionic acid, methacrolein dimer, 2-methyl-2-pentenal, and other methacrolein oligomers) that can have a negative effect on efficiency of the OER process.

Processes for preparing dry MA have been described in the art. For example, US 2016/0229779 discloses a process comprising (a) providing a wet MA stream containing MA, methanol, and at least 8 weight % water to a phase separator, (b) separating the MA stream into organic and aqueous phases, (c) distilling the organic phase to produce a product stream containing MA and a first overhead stream, (d) sending the first overhead stream back to the phase separator, and (e) distilling the aqueous phase to produce a second overhead stream that is recycled back to the phase separator. The prior art does not, however, disclose a process that further maximizes methanol capture for use in a downstream OER process, or further minimizes certain impurities that can negatively affect the efficiency of the OER process.

Accordingly, there is a need to develop processes for drying wet MA prepared from an ethylene ($C_2$) feedstock, wherein methanol is efficiently captured for a downstream OER process while also removing detrimental impurities.

STATEMENT OF INVENTION

A process for preparing methacrolein comprising (a) mixing water and an amine-acid catalyst to provide a catalyst stream [10], (b) sending the catalyst stream and a reaction stream [20] comprising propionaldehyde, formaldehyde, and methanol to a reactor [200] to produce a first intermediate stream [30] comprising methacrolein, methanol, and at least 8 weight % water, (c) providing the first intermediate stream [30] to a phase separator [300] to produce (i) an organic phase [40] comprising (A) less than 4 weight % water, and (B) at least 70 weight % methacrolein, and (ii) an aqueous phase [50] comprising methacrolein, methanol, amine-acid catalyst, and at least 70 weight % water, wherein the phase separator [300] is operated at a temperature of less than 25° C., (d) distilling the organic phase in a first distillation column [400] to produce (i) a first product stream [60] comprising (A) methacrolein and methanol in a combined amount of at least 95 weight %, (B) less than 4 weight % water, and (C) less than 1 weight % of impurities comprising one or more of acetic acid, propionic acid, methacrolein dimer, and 2-methyl-2-pentenal, and (ii) a first waste stream [41], (e) distilling the aqueous phase [50] in a second distillation column [500] to produce (i) a second product stream [70] comprising methacrolein, methanol, and less than 5 weight % water, (ii) a bottoms stream [51] comprising amine-acid catalyst, and (iii) a side draw stream [52] comprising water and less than 2 weight % methanol, and (h) recycling at least part of the bottoms stream [51] to the catalyst stream [10].

In another aspect of the invention, the propionaldehyde is produced by contacting ethylene with CO and $H_2$ in the presence of a hydroformylation catalyst.

Another aspect of the invention further comprises providing at least part of the first product stream and at least part of the second product stream to a process comprising contacting the methacrolein with methanol and an oxygen-containing gas in the presence of an oxidative esterification catalyst to produce methyl methacrylate.

BRIEF DESCRIPTION OF THE FIGURES

FIG. 1 is a schematic of an embodiment of the invention.

DETAILED DESCRIPTION

The inventors have now surprisingly found a process for drying wet methacrolein ("MA") prepared from an ethylene ($C_2$) feedstock, wherein methanol is efficiently captured for a downstream oxidative esterification reaction ("OER") process while also removing detrimental impurities.

One embodiment of the invention is shown in FIG. 1. A catalyst stream 10 is provided by mixing water and an amine-acid catalyst. In certain embodiments, the water and catalyst are mixed in a catalyst tank 100. The amine-acid catalyst is capable of catalyzing the Mannich condensation of propionaldehyde and formaldehyde to methacrolein. The Mannich condensation process is known in the art, for example, as described in U.S. Pat. Nos. 4,496,770 and 7,141,702. Suitable amine-acid catalysts include, for example, those comprising a secondary amine, e.g., dimethylamine, and an acid, e.g., acetic acid.

Suitable acids of the amine-acid catalysts include, for example, inorganic acids and organic mono-, di-, or polycarboxylic acids. Suitable carboxylic acids include, for example, aliphatic $C_1$-$C_{10}$ monocarboxylic acids, $C_2$-$C_{10}$ dicarboxylic acids, $C_2$-$C_{10}$ polycarboxylic acids. In certain embodiments, the acid comprises at least one of acetic acid, propionic acid, methoxyacetic acid, n-butyric acid, isobutyric acid, oxalic acid, succinic acid, tartaric acid, glutaric acid, adipic acid, maleic acid, fumaric acid, and combinations thereof. Suitable inorganic acids include, for example, sulfuric acid and phosphoric acid.

Suitable amines of the amine-acid catalysts include, for example, those of the formula $NHR^2R^3$, where $R^2$ and $R^3$ are each independently $C_1$-$C_{10}$ alkyl, which are optionally substituted with an ether, hydroxyl, secondary amino or tertiary amino group, or $R^2$ and $R^3$, together with the adjacent nitrogen, may form a $C_5$-$C_7$ heterocyclic ring, optionally containing a further nitrogen atom and/or an oxygen atom, and which are optionally substituted by a $C_1$-$C_4$ alkyl or $C_1$-$C_4$ hydroxyalkyl. In certain embodiments, the amine comprises at least one of dimethylamine, diethylamine, methylethylamine, methylpropylamine, dipropylamine, dibutylamine, diisopropylamine, diisobutylamine, methylisopropylamine, methylisobutylamine, methyl-sec.-butylamine, methyl-(2-methylpentyl)-amine, methyl-(2-ethylhexyl)-amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, and dicyclohexylamine, and combinations thereof.

In certain embodiments, the amine-acid catalyst comprises dimethylamine and acetic acid. In certain embodiments, the molar ratio of the amine to acid is such that the resulting pH is from 2.5 to 7. For example, in certain embodiments the amine-acid catalyst contains a molar ratio of dimethylamine to acetic acid in an amount of from 10:1 to 1:10, preferably of from 5:1 to 1:5, and more preferably of from 1:1 to 1:1.2.

The Mannich condensation reaction is carried out by sending the catalyst stream 10 and a reaction stream 20 containing propionaldehyde, formaldehyde, and methanol to a reactor 200 to produce a first intermediate stream 30 containing methacrolein, methanol, and water via the Mannich condensation reaction. The reaction can be carried out under any suitable conditions at which the reaction proceeds. For example, the reaction can be conducted at a temperature of at least 20° C. and at least atmospheric pressure. In certain embodiments, the reaction is conducted in the liquid phase at above 100° C., e.g., 150-220° C., at superatmospheric pressure, e.g., 10-80 bar, and reactor residence times between 0.01 to 30 minutes. The molar ratio of propionaldehyde to formaldehyde is not particularly limited. For example, in certain embodiments the reaction stream 20 contains a ratio of propionaldehyde to formaldehyde in an amount of from 1.1:1 to 1:2, preferably of from 1.1:1 to 1:1.5, and more preferably of from 1.05:1 to 1:1.05. The first intermediate stream 30 is considered a "wet" methacrolein stream in that it comprises at least 8 weight %, or at least 10 weight % water, or at least 20 weight % water, or at least 40 weight % water, based on the total weight of the first intermediate stream 30. In certain embodiments, the methanol and formaldehyde present in the reaction stream 20 are provided in the form of formalin. In certain embodiments, the formalin utilized in the process of the invention is a saturated water solution containing formaldehyde in an amount of about 37 weight %, and methanol in an amount of from 10 to 15 weight %, based on the total weight of the formalin. The methanol present in the formalin can be advantageous in a subsequent oxidative esterification process, which converts methacrolein in the presence of methanol to methyl methacrylate. In certain embodiments, methanol can be introduced at various locations in the process. The inventors have surprisingly found that the efficient capture of methanol from the first intermediate feed stream 30 used as a source for the subsequent oxidative esterification process is beneficially achieved by the process of the current invention.

Accordingly, the first intermediate stream 30 is sent to a phase separator 300 to produce an organic phase 40 and aqueous phase 50. The organic phase 40 contains water, methanol, and primarily methacrolein. In certain embodiments, the methacrolein is present in the organic phase 40 in an amount of at least 70 weight %, preferably at least 85 weight %, and more preferably at least 90 weight %, based on the total weight of the organic phase 40. In certain embodiments, the methanol is present in the organic phase 40 in an amount of less than 10 weight %, preferably less than 3 weight %, and more preferably less than 2.5 weight %, based on the total weight of the organic phase 40. In certain embodiments, water is present in the organic phase 40 in an amount of less than 4 weight %, preferably less than 3 weight %, and more preferably less than 2 weight %, based on the total weight of the organic phase. While not wishing to be bound by theory, it is believed that operating the phase separator 300 at low temperatures results in the organic phase 40 containing lower amounts of water, which is beneficial for any downstream oxidative esterification process. Accordingly, in certain embodiments the phase separator 300 is operated at a temperature of less than 15° C., preferably less than 10° C., and more preferably less than 5° C. The aqueous phase 50 contains methacrolein, methanol, amine-acid catalyst, and primarily water. In certain embodiments, water is present in the aqueous phase 50 in an amount of at least 70 weight %, preferably at least 75 weight %, and more preferably at least 80 weight %, based on the total weight of the aqueous phase 50.

The organic phase 40 is then distilled in a first distillation column 400 to produce a first product stream 60 and waste stream 41. The first product stream 60 contains water, methanol, and primarily methacrolein. In certain embodiments, the methacrolein is present in the first product stream 60 in an amount of at least 70 weight %, preferably at least 85 weight %, and more preferably at least 95 weight %, based on the total weight of the first product stream 60. In certain embodiments, methanol is present in the first product stream 60 in an amount of less than 30 weight %, preferably less than 10 weight %, and more preferably less than 2 weight %, based on the total weight of the first product stream 60. In certain embodiments, the methacrolein and methanol are present in the first product stream 60 in a combined amount of at least 95 weight %, preferably at least 96 weight %, and more preferably at least 97 weight %. In certain embodiments, water is present in the first product stream 60 in an amount of less than 4 weight %, preferably less than 3 weight %, and more preferably less than 2 weight %, based on the total weight of the first product stream 60. In certain embodiments, the first product stream 60 contains impurities comprising one or more of acetic acid, propionic acid, methacrolein dimer, and 2-methyl-2-pentenal in a combined amount of less than 1 weight %, preferably less than 0.5 weight %, and more preferably less than 0.2 weight %, based on the total amount of the product stream 60. The waste stream 41 contains undesired organic compounds from the process, e.g., methacrolein dimer, 2-methyl-2-pentenal, inhibitor, and other heavy organic compounds from the process.

The aqueous phase 50 is distilled in a third distillation column 500 to produce a second product stream 70, a bottoms stream 51, and a side draw stream 52. The second product stream 70 contains water, methanol, and methacrolein. In certain embodiments, water is present in the second product stream 70 in an amount of less than 5 weight %, preferably less than 2 weight %, and even more preferably less than 1 weight %, based on the total weight of the second product stream 70. In certain embodiments, methacrolein is present in the second product stream 70 in an amount of greater than 25 weight %, preferably greater than 35 weight %, and more preferably greater than 45 weight %, based on the total weight of the second product stream 70. In certain embodiments, methanol is present in the second product stream 70 in an amount of greater than 25 weight %, preferably greater than 40 weight %, and more preferably greater than 55 weight %, based on the total weight of the second product stream 70. The bottoms stream 51 contains amine-acid catalyst of the catalyst stream 10 that is recovered through the process of the invention. In certain embodiments, at least part of the bottoms stream 51 is recycled to the catalyst stream 10, which in preferred embodiments is mixed in the catalyst tank 100. The side draw stream 52 contains primarily water and certain organic compounds from the process. In certain embodiments, the side draw stream 52 contains methanol in an amount of less than 2 weight %, preferably less than 1.5 weight %, and more preferably less than 1 weight %.

Inhibitors can be introduced into the process through one or more locations, for example, the catalyst tank 100, the reactor 200, the phase separator 300, the first distillation column 400, the second distillation column 500, the first product stream 60, and the second product stream 70. Suitable inhibitors include, for example, 4-hydroxy-2,2,6,6-tetramethylpiperidin-1-oxyl (4-Hydroxy-TEMPO).

In certain embodiments, the propionaldehyde in the reaction stream 10 is prepared by the hydroformylation of ethylene. The hydroformylation process is known in the art, for example, as described in U.S. Pat. Nos. 4,427,486, 5,087,763, 4,716,250, 4,731,486, and 5,288,916. The hydroformylation of ethylene to propionaldehyde involves contacting ethylene with CO and hydrogen in the presence of a hydroformylation catalyst. Suitable hydroformylation catalysts include, for example, metal-organophosphorous ligand complexes. Suitable organophosphorous ligands include, for example, organophosphines, organophosphites, and organophosphoramidites. In certain embodiments, the ratio of CO to hydrogen is in the range of from 1:10 to 100:1, preferably of from 1:10 to 10:1. In certain embodiments, the hydroformylation reaction is conducted at a reaction temperature of from −25° C. to 200° C., preferably of from 50° C. to 120° C.

In certain embodiments, either or both of the first product stream 60 and second product stream 70 are utilized in a downstream oxidative esterification ("OER") process. The OER process comprises contacting the methacrolein with methanol and an oxygen containing gas in the presence of an oxidative esterification catalyst under reaction conditions sufficient to produce methyl methacrylate. The OER process is known in the art, for example, as described in U.S. Pat. Nos. 5,969,178, 6,107,515, 5,892,102, 4,249,019, and 4,518,796. In certain embodiments the methacrolein and methanol are supplied to the OER process by the first product stream 60. In certain embodiments, the methacrolein and methanol are supplied to the OER process by the second product stream 70. In certain embodiments the methacrolein and methanol are supplied to the OER process by the first product stream 60 and the second product stream 70. The low amounts of water in each of the first product stream 60 and second product stream 70 makes each of the streams particularly advantageous as a source feed for the OER process. Furthermore, the methanol recovered from the process in the second product stream 70 also makes it particularly advantageous as a source feed for the OER process. The molar ratio of methanol to methacrolein employed in the OER process is not particularly limited, and may be conducted over a wide range of molar ratios such as from 1:10 to 1,000:1, preferably from 1:1 to 10:1. Oxygen-containing gases that are suitable for the OER process include, for example, oxygen gas, or a mixed gas comprising oxygen gas and a diluent inert to the reaction (e.g., nitrogen, carbon dioxide, and the like). In certain embodiments, air may be utilized as a suitable oxygen-containing gas for the OER process. Suitable OER catalysts include, for example, palladium-based catalysts, gold-based catalysts, and intermetallics containing combinations of two or more metals. The catalytic elements maybe supported on a carrier, for example, silica or alumina. In certain embodiments, the OER process is conducted at a reaction temperature of from 0° C. to 120° C., preferably of from 40° C. to 90° C.

Some embodiments of the invention will now be described in detail in the following Examples.

EXAMPLES

Example 1

Preparation of Methacrolein

A static mixer 29″ long and 0.1315″ inner diameter was used as a reactor. Dimethyl amine, acetic acid and water were mixed in a catalyst mixing vessel from which the outlet flow was 550 g/h containing 4.5 weight % dimethyl amine and an amount of acetic acid sufficient to maintain stream pH at 5.5. A stream comprising propionaldehyde and 37 weight % formaldehyde solution in water also containing 10-15% methanol (1:1 propionaldehyde:formaldehyde molar ratio) at a total flow of 1575 g/h was mixed with the aqueous catalyst solution and added to the reactor which was heated to 160° C. and maintained at 900 psig. An inhibitor solution containing 8 weight % 4-Hydroxy-TEMPO in water was added to the reactor at a flow rate of 20 g/h. The reactor outlet was cooled to 25° C., depressurized to 1 atm and sent to a phase separator with an internal temperature of 7° C. and pressure of 1 atm. The organic phase flow rate from the phase separator was 705 g/h and it contained 94 weight % methacrolein, 3.2 weight % water, and 1.6 weight % methanol. The organic phase was sent to a distillation column with 22 trays wherein the distillate was sent to a downstream oxidative esterification process and the bottoms stream was sent to waste. An inhibitor solution containing 8 weight % 4-Hydroxy-TEMPO in methanol was added to the condenser of the distillation column at a flow rate of 10 g/h. The distillate consisted of 93 weight % methacrolein, 3.9 weight % water, 3.3 weight % methanol, and less than 0.2 weight % combined undesired impurities (e.g., acetic acid, propionic acid, methacrolein dimer, and 2-methyl-2-pentenal). The bottoms stream flow rate from this column was 30 g/h. The aqueous phase contained 84 weight % water and was sent to a distillation column with 30 trays. The distillate flow from this column was 230 g/h consisting of 54 weight % methanol, 46 weight % methacrolein, and 0.1 weight % water, which was sent to a downstream oxidative esterification process. An inhibitor solution containing 8 weight % 4-Hydroxy-TEMPO in methanol was added to the condenser of the distillation column at a flow rate of 8 g/h. The side-draw flow from the distillation column was 715 g/h comprising primarily water and 0.8 weight % methanol. An inhibitor solution containing 8 weight % 4-Hydroxy-TEMPO in methanol was added to the side-draw receiver of the distillation column at a flow rate of 2 g/h. The bottoms stream from the distillation column contained primarily water and the recovered amine-acid catalyst. A fraction of 0.9 of the bottoms stream from the distillation column was recycled to the catalyst mixing vessel.

The example demonstrates that the process of this invention is effective at producing a methacrolein product stream with a low concentration of water, low concentration of undesired impurities, while also effectively capturing methanol contained in the formalin feedstock for use in a downstream oxidative esterification process to a level not previously achieved by the various methods of the prior art.

What is claimed is:

1. A process for preparing methacrolein comprising:
   (a) mixing water and an amine-acid catalyst to provide a catalyst stream;
   (b) sending the catalyst stream and a reaction stream comprising propionaldehyde, formaldehyde, and methanol to a reactor to produce a first intermediate stream comprising methacrolein, methanol, and at least 8 weight % water;
   (c) providing the first intermediate stream to a phase separator to produce (i) an organic phase comprising (A) less than 4 weight % water, and (B) at least 70 weight % methacrolein, and (ii) an aqueous phase comprising methacrolein, methanol, amine-acid catalyst, and at least 70 weight % water, wherein the phase separator is operated at a temperature of less than 25° C.;
   (d) distilling the organic phase in a first distillation column to produce (i) a first product stream comprising (A) methacrolein and methanol in a combined amount of at least 95 weight %, (B) less than 4 weight % water, and (C) less than 1 weight % of impurities comprising one or more of acetic acid, propionic acid, methacrolein dimer, and 2-methyl-2-pentenal, and (ii) a first waste stream;
   (e) distilling the aqueous phase in a second distillation column to produce (i) a second product stream comprising methacrolein, methanol, and less than 5 weight % water, (ii) a bottoms stream comprising amine-acid catalyst, and (iii) a side draw stream comprising water and less than 2 weight % methanol; and
   (h) recycling at least part of the bottoms stream to the catalyst stream.

2. The process of claim 1, wherein the propionaldehyde is produced by contacting ethylene with CO and $H_2$ in the presence of a hydroformylation catalyst.

3. The process of claim 1, further comprising providing at least part of the first product stream to a process comprising contacting the methacrolein with methanol and an oxygen-containing gas in the presence of an oxidative esterification catalyst to produce methyl methacrylate.

4. The process of claim 1, further comprising providing at least part of the second product stream to a process comprising contacting the methacrolein with methanol and an oxygen-containing gas in the presence of an oxidative esterification catalyst to produce methyl methacrylate.

5. The process of claim 1, further comprising providing at least part of the first product stream and at least part of the second product stream to a process comprising contacting the methacrolein with methanol and an oxygen-containing gas in the presence of an oxidative esterification catalyst to produce methyl methacrylate.

6. The process of claim 2, further comprising providing at least part of the first product stream and at least part of the second product stream to a process comprising contacting the methacrolein with methanol and an oxygen-containing gas in the presence of an oxidative esterification catalyst to produce methyl methacrylate.

7. The process of claim 1, wherein the organic phase comprises less than 10 weight % methanol.

8. The process of claim 1, wherein the phase separator is operated at a temperature of less than 5° C.

* * * * *